(12) United States Patent
Patwardhan

(10) Patent No.: US 10,656,150 B2
(45) Date of Patent: May 19, 2020

(54) SYSTEMS AND METHODS FOR A LATERAL FLOW TEST STRIP HOLDER

(71) Applicant: Polymer Technology Systems, Inc., Indianapolis, IN (US)

(72) Inventor: Aniruddha Patwardhan, Fishers, IN (US)

(73) Assignee: POLYMER TECHNOLOGY SYSTEMS, INC., Whitestown, IN (US)

(*) Notice: Subject to any disclaimer, the term of this patent is extended or adjusted under 35 U.S.C. 154(b) by 307 days.

(21) Appl. No.: 15/277,525

(22) Filed: Sep. 27, 2016

(65) Prior Publication Data

US 2017/0087549 A1 Mar. 30, 2017

Related U.S. Application Data

(60) Provisional application No. 62/234,528, filed on Sep. 29, 2015.

(51) Int. Cl.
| | |
|---|---|
| *G01N 33/558* | (2006.01) |
| *G01N 21/84* | (2006.01) |
| *B01L 3/00* | (2006.01) |
| *G01N 21/78* | (2006.01) |
| *G01N 33/52* | (2006.01) |
| *G01N 21/77* | (2006.01) |

(52) U.S. Cl.
CPC .......... *G01N 33/558* (2013.01); *B01L 3/5023* (2013.01); *G01N 21/78* (2013.01); *G01N 21/8483* (2013.01); *G01N 33/521* (2013.01); *B01L 2200/027* (2013.01); *B01L 2300/041* (2013.01); *B01L 2300/0609* (2013.01); *B01L 2300/069* (2013.01); *B01L 2300/0627* (2013.01); *B01L 2400/0406* (2013.01); *G01N 2021/7759* (2013.01)

(58) Field of Classification Search
CPC .. G01N 33/558; G01N 21/8483; G01N 21/78; G01N 33/521; B01L 3/5023
See application file for complete search history.

(56) References Cited

U.S. PATENT DOCUMENTS

| | | | |
|---|---|---|---|
| 6,365,417 B1 * | 4/2002 | Fleming | G01N 33/558 422/412 |
| 2004/0029177 A1 * | 2/2004 | Nadaoka | G01N 33/558 435/7.1 |
| 2004/0142398 A1 * | 7/2004 | Bandla | G01N 33/558 435/7.32 |
| 2004/0241881 A1 | 12/2004 | Kuriger | |
| 2004/0247491 A1 | 12/2004 | Brock et al. | |
| 2006/0008847 A1 * | 1/2006 | Ramel | B01L 3/5023 435/7.1 |
| 2008/0112848 A1 | 5/2008 | Huffstodt et al. | |

(Continued)

OTHER PUBLICATIONS

International Search Report and Written Opinion dated Dec. 19, 2016 issued in co-pending PCT App. No. PCT/US2016/053948 (13 pages).

(Continued)

*Primary Examiner* — Melanie Brown
(74) *Attorney, Agent, or Firm* — Haynes and Boone, LLP

(57) ABSTRACT

A system of detecting a blood analyte includes a lateral flow test strip and a test strip holder, the lateral flow test strip located in the test strip holder. The system further includes a meter for receiving the test strip holder.

16 Claims, 6 Drawing Sheets

(56) References Cited

U.S. PATENT DOCUMENTS

| | | | |
|---|---|---|---|
| 2008/0289068 A1* | 11/2008 | Danks | G01N 33/558 800/298 |
| 2011/0155590 A1 | 6/2011 | Huffstodt et al. | |
| 2013/0162981 A1 | 6/2013 | Emeric et al. | |
| 2013/0184188 A1 | 7/2013 | Ewart et al. | |
| 2013/0217054 A1 | 8/2013 | Huffstodt et al. | |
| 2014/0295406 A1 | 10/2014 | Sundvor et al. | |
| 2015/0079668 A1* | 3/2015 | Kobayashi | G01N 33/558 435/287.2 |

OTHER PUBLICATIONS

Extended European Search Report dated Feb. 19, 2019 issued in corresponding European Patent App. No. 16852408.0 (13 pages).
Notice of Intention to Grant dated Feb. 18, 2020 issued in corresponding European Patent App. No. 16852408.0 (19 pages).

* cited by examiner

SYSTEMS AND METHODS FOR A LATERAL FLOW TEST STRIP HOLDER

CROSS REFERENCE TO RELATED APPLICATION

This application claims the benefit of U.S. Provisional Patent Application No. 62/234,528 filed Sep. 29, 2015, and hereby incorporated by reference to the same extent as though fully disclosed herein.

BACKGROUND

Various systems exist for point-of-care testing of blood analytes. Many systems for testing for blood analytes include a lateral flow test strip. Such lateral flow test strips typically require a cassette or other type of holder in order to support the test strip and allow for handling by the user without contamination. It is desirable to have a test strip holder that requires minimum material and can interface well with meters and other devices.

BRIEF SUMMARY

In one embodiment, a system of detecting a blood analyte includes a lateral flow test strip and a test strip holder, the lateral flow test strip located in the test strip holder. The system further includes a meter for receiving the test strip holder. Optionally, the system further includes a wicking membrane located in the test strip holder. Alternatively, the test strip holder includes a lid and a base. In one alternative, the lid includes a dosing window, and the wicking membrane is located under the dosing window. In another alternative, the base includes a reading window. Optionally, the base includes a base cavity that receives the lateral flow test strip and the wicking membrane. Alternatively, the base cavity includes a ledge that causes a sample to flow toward the lateral flow test strip from the wicking membrane. In one configuration, the lid is flush with a top of the lateral flow test strip when the lid is engaged with the base, such that excess fluid may not flow on top of the lateral flow test strip. In another configuration, the lid interfaces with the base in a pressure fit arrangement. Optionally, the lid includes wings and snaps into the base. Alternatively, an underside of the lid includes ribs for holding the lateral flow test strip in place. In one alternative, the lid compresses the lateral flow test strip into the base. In another alternative, the meter includes a slot for receiving the lateral flow test strip and test strip holder combination, and the reading window aligns with a sensor of the meter.

In one embodiment, a test strip assembly includes a lateral flow test strip and a test strip holder, the lateral flow test strip located in the test strip holder. Optionally, the system further includes a wicking membrane located in the test strip holder. Alternatively, the test strip holder includes a lid and a base. Optionally, the lid includes a dosing window, and the wicking membrane is located under the dosing window. In one configuration, the base includes a reading window. In another configuration, the base includes a base cavity that receives the lateral flow test strip and the wicking membrane. Optionally, the base cavity includes a ledge that causes a sample to flow toward the lateral flow test strip from the wicking membrane. Alternatively, the lid is flush with a top of the lateral flow test strip when the lid is engaged with the base, such that excess fluid may not flow on top of the lateral flow test strip. Optionally, the lid interfaces with the base in a pressure fit arrangement. In one alternative, the lid includes wings and snaps into the base. In another alternative, an underside of the lid includes ribs for holding the lateral flow test strip in place. Optionally, the lid compresses the lateral flow test strip into the base.

In one embodiment, a method of testing for a blood analyte includes providing a test strip assembly, including a lateral flow test strip and a test strip holder, the lateral flow test strip located in the test strip holder. The method further includes introducing a sample to the lateral flow test strip. The method further includes flowing the sample along the lateral flow test strip, producing a colored response to the sample, and measuring the colored response with a meter.

DETAILED DESCRIPTION

Figure 1:
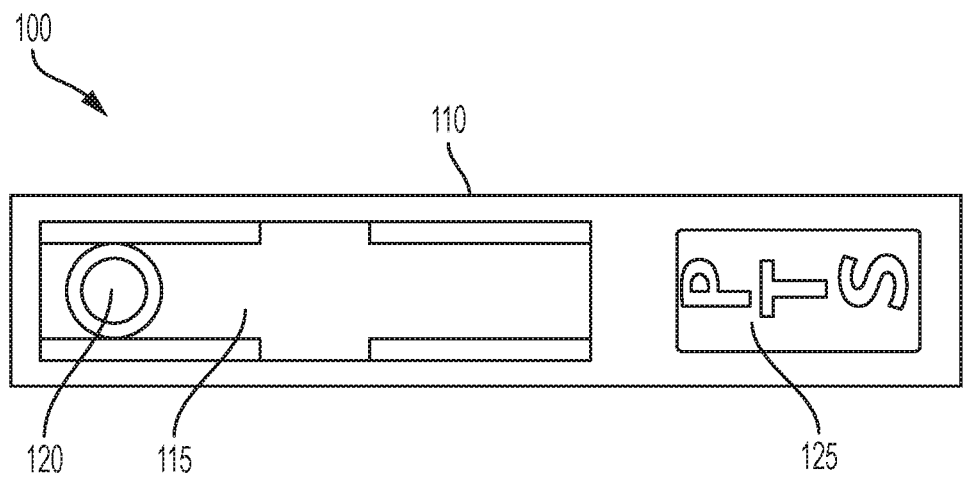
FIGS. 1 and 2 show one embodiment of a test strip holder including a lateral flow test strip.

Certain terminology is used herein for convenience only and is not to be taken as a limitation on the embodiments of the systems and methods for a lateral flow test strip holder. In the drawings, the same reference letters are employed for designating the same elements throughout the several figures. The system presented provides for a test strip holder that can fit with a meter instead of a cassette, which is typically more cost effective, since test strip holders may be smaller and use less material, therefore reducing the cost.

Embodiments include a novel test strip design where a lateral flow membrane is accommodated. In some embodiments, the design is such that its footprint fits in the optical block of the CardioChek® Plus Analyzer. The strip uses the already existing features of the CardioChek® platform.

Embodiments of the test strip holder design provide for the opportunity for lateral flow test strips to be used with meters that currently do not receive lateral flow test strips because they are designed to receive cassettes. Specifically, in relation to some embodiments, currently an HbA1c and cotinine assays are offered in a lateral flow format by Polymer Technology Systems, Inc. (PTS). The system includes a lateral flow test strip that is in a cassette. Instead, the lateral flow test strips may be migrated to a test strip which allows it to be received by meters typically designed for vertical flow test strips, such as the CardioChek® series of meters designed by Polymer Technology Systems, Inc. The CardioChek® Plus meter provides for many features that may be desirable to integrate into a meter, including wireless communication, Bluetooth communication, a printer, and access to Health Risk Assessment programs offered by Polymer Technology Systems, Inc.

Additionally, embodiments of lateral flow test strips in test strip holders provide for reduced sample requirement;

therefore, the buffer volume requirement in the sampler is reduced, resulting in additional cost savings.

Figure 2:
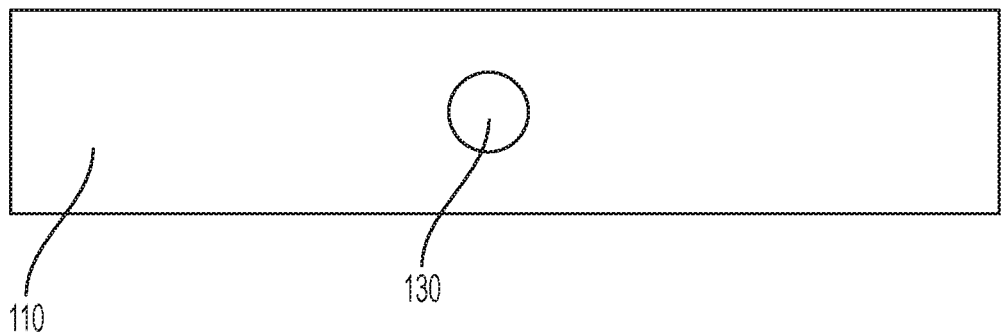

FIGS. 1 and 2 show one embodiment of a test strip holder including a lateral flow test strip. The lid and cavity of the test strip holder have been designed to accommodate the lateral flow test strip. The test strip holder and test strip include a dosing window, a wicking membrane, and a lateral flow membrane. FIG. 1 shows one embodiment of a test strip assembly 100. The test strip assembly 100 includes a base 110 and a lid 115. Lid 115 includes a dosing window 120. A logo section 125 also is included. Logo section 125 also is useful for holding test strip assembly 100. FIG. 2 shows a bottom side view of one embodiment of the base 110 of the holder. The base includes a read window 130 for reading a color change with a meter.

Figure 3:
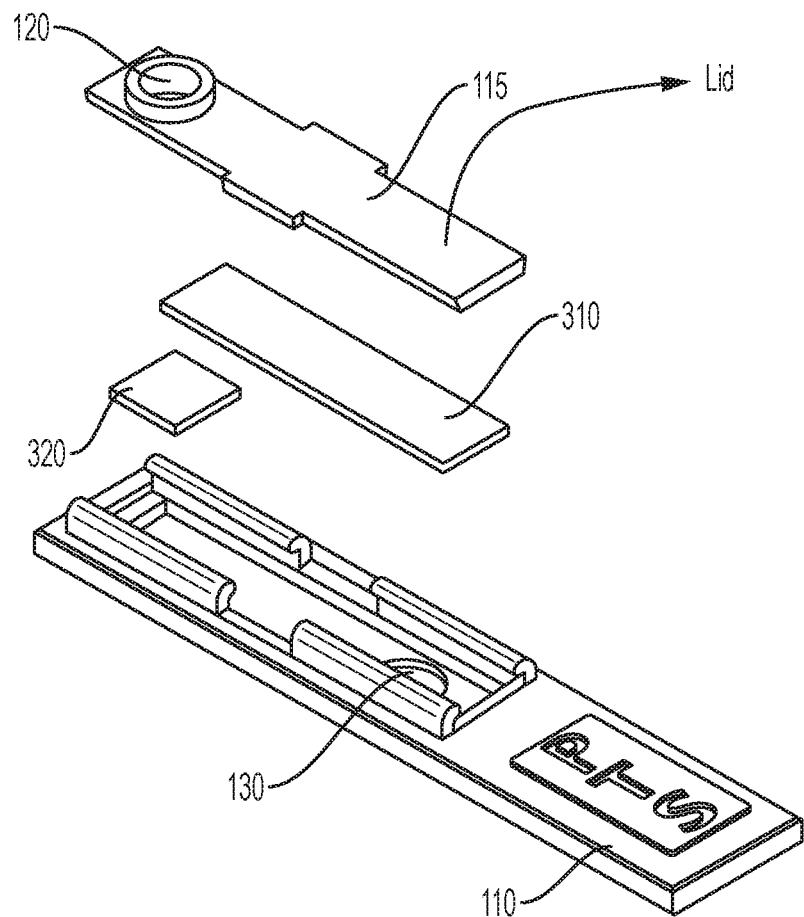
FIG. 3 shows an exploded view of the test strip assembly of FIG. 1.

FIG. 3 shows an exploded view of the test strip assembly 100. The lid 115 and the base 110 are shown. Additionally, the lateral flow membrane 310 and wicking pad 320 are shown. The relation between the dosing window, wicking membrane, and the lateral flow membrane assembly is shown in a cross-sectional image (see FIG. 3).

Figure 4:
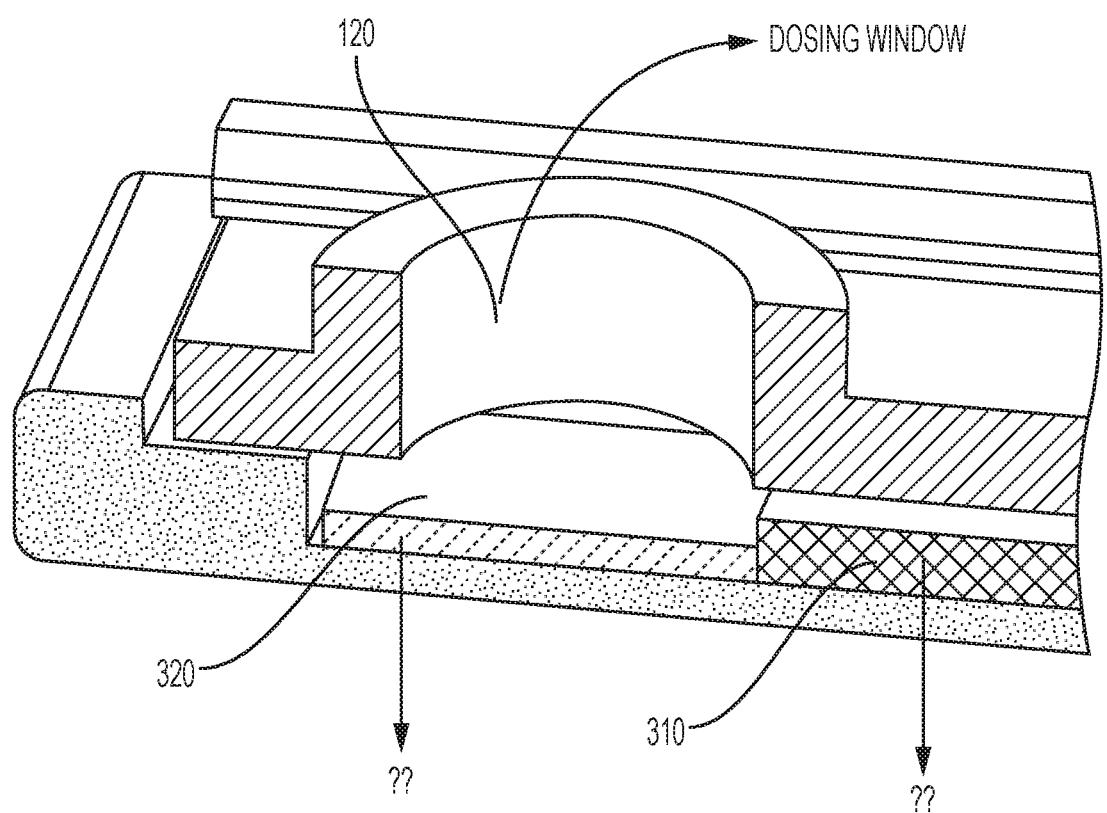
FIG. 4 shows a cut-away view of the test strip assembly of FIG. 1.

As is visible in FIG. 4, the wicking pad 320 is aligned with the dosing window 120 of the lid 115. Additionally, the vertical alignment of the wicking pad 320 and the lateral flow membrane 310 is shown.

Figure 5:
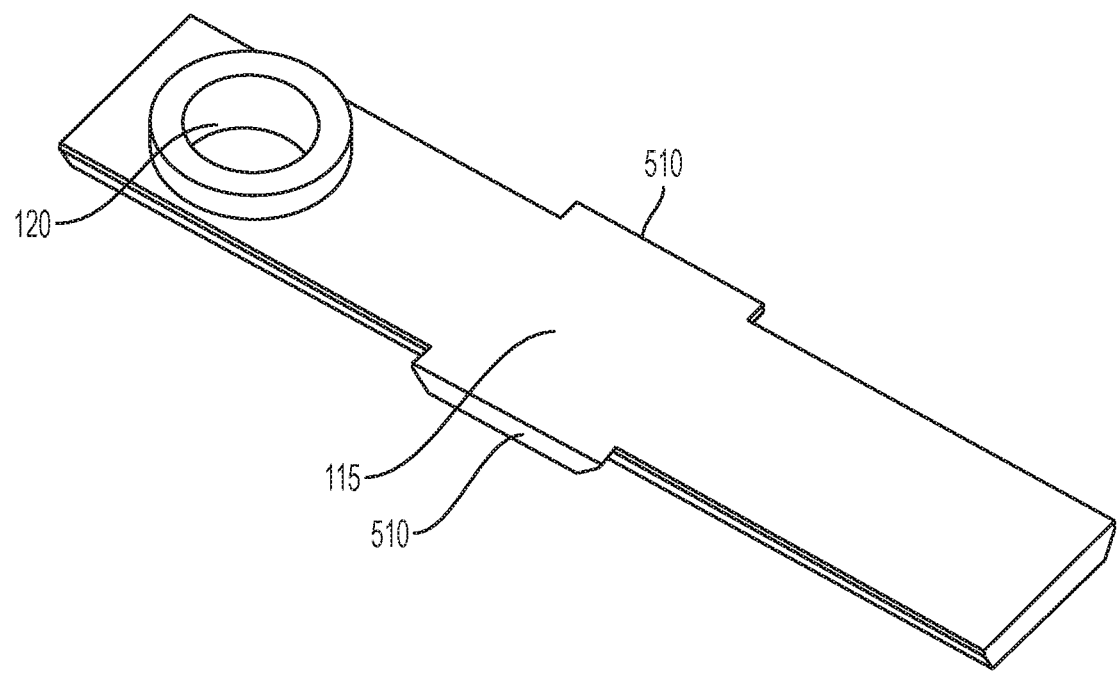
FIG. 5 shows one embodiment of the lid of the test strip assembly.

FIG. 5 shows one embodiment of the lid 115 of the test strip assembly 100. The lid is designed to allow dosing at the distal end of the test strip. The lid snaps into the base 110 with beveled "wings" 510 for ease of manufacturability. The sample port opening, or dosing window 120, is 0.125 in (3.175 mm) in diameter and with a depth of 0.071 in (1.8 mm) yielding total volume of (0.179 cu mm). The depth of the dosing window 120 can be altered to accommodate a larger volume of sample. The placement of the lid 115 on the test strip assembly 100 can be achieved through a simple pick and place automated mechanism. Another feature is that the bottom of the lid 115 (not shown) has four small ribs or ridges that allow for "holding down" the lateral flow membrane in place and does not allow it to "slip". Importantly, the cap or lid 115 provides the correct compression to allow efficient wicking of the sample and attain a response in a reasonable amount of time.

Figure 6:
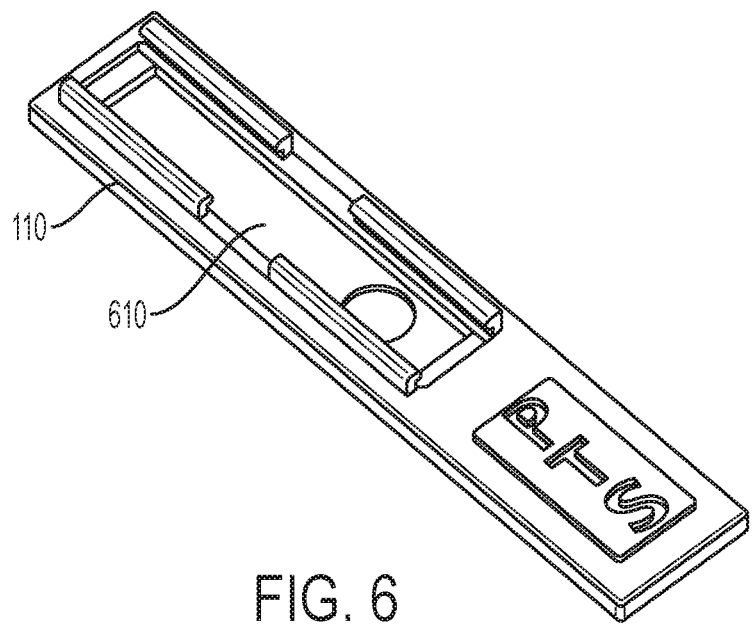
FIGS. 6 and 7 show one embodiment of the base of the test strip assembly.
Figure 7:
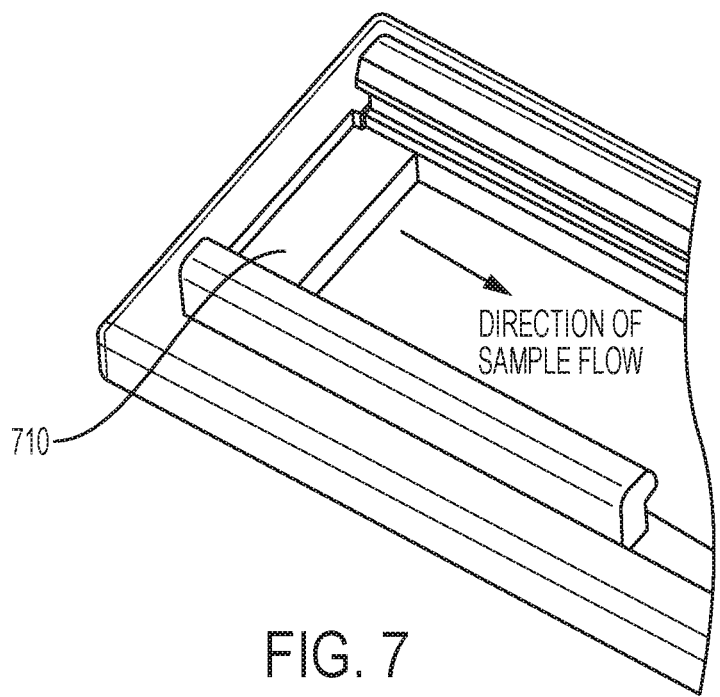

FIGS. 6 and 7 show one embodiment of base 110. The base 110 length is 1.8 in (45.72) and width is 0.37 in (9.39 mm) which fits the optical block assembly in the current CardioChek® meters, although in alternative embodiments, any meter configuration can be used. The base cavity 610 in which the lateral flow test strip 310 and the wicking membrane 320 will reside is 0.961 inches (24.04 mm) in length and has a width of 0.185 in (4.7 mm). The base has a ledge 710 (see FIG. 7) which allows the flow of fluid in only one direction, which is toward the lateral flow test strip assembly.

Figure 8:
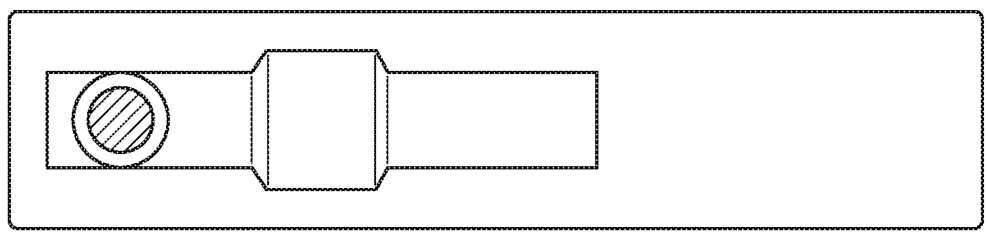
FIG. 8 shows one embodiment of a strip dosed with 15 µL of whole blood.
Figure 9:
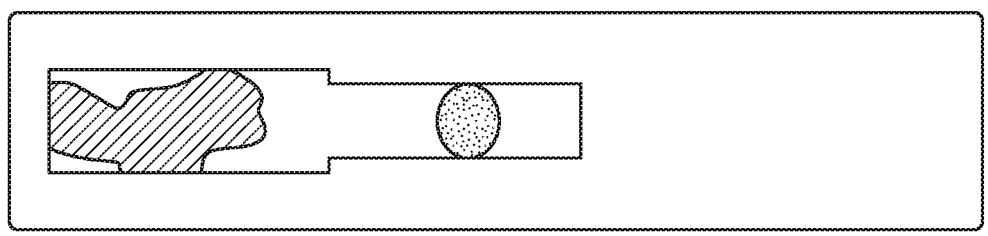
FIG. 9 shows the back side of the strip of FIG. 8 showing the position of the blue particles when dosed with whole blood.

A prototype test was performed with the above embodiment. Prototypes were created, and these prototypes showed that the lateral flow test strips from the PTS cotinine assay were capable of being imported and provide percent reflectance reading. The base was purposely made of transparent plastic to observe and determine the fluid movement in the strip. FIG. 8 shows one embodiment of a strip dosed with 15 µL of whole blood (no dilution required). FIG. 9 shows the back side of the strip showing the position of the blue particles when dosed with whole blood.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof. Note that, although particular embodiments are shown, features of each may be interchanged between embodiments.

What is claimed as new and desired to be protected by Letters Patent of the United States is:

1. A system of detecting a blood analyte, comprising:
   a test strip holder, the test strip holder comprising a base defining a base cavity having a first end and a second end, the base defining a reading window adjacent the second end of the base cavity, the test strip holder further comprising a lid secured to the base over the base cavity, the lid defining a dosing window adjacent the first end of the base cavity;
   a wicking membrane received within the base cavity adjacent the first end of the base cavity and aligned under the dosing window;
   a lateral flow test strip received within the base cavity, the lateral flow test strip having a dosing end and a testing end, the dosing end being positioned against the wicking membrane, such that an edge of the lateral flow test strip is in line with an edge of the dosing window; and
   a meter receiving the test strip holder, the meter including a sensor, wherein the lid is flush with the lateral flow test strip, such that fluid may not flow between the lid and the lateral flow test strip.

2. The system of claim 1, wherein the base cavity includes a ledge at the first end of the base cavity, the wicking membrane being positioned between the ledge and the lateral flow test strip, the ledge causing a sample to flow toward the lateral flow test strip from the wicking membrane.

3. The system of claim 1, wherein the lid interfaces with the base in a pressure fit arrangement.

4. The system of claim 3, wherein the lid includes wings and snaps into the base.

5. The system of claim 1, wherein the underside of the lid includes ribs for holding the lateral flow test strip in place.

6. The system of claim 5, wherein the lid compresses the lateral flow test strip into the base.

7. The system of claim 1, wherein the meter includes a slot for receiving the test strip holder and the reading window aligns with the sensor of the meter.

8. The test strip assembly of claim 1, wherein a bottom side of the wicking membrane is aligned with a bottom side of the lateral flow test strip and a top side of the wicking membrane is lower than a top side of the lateral flow test strip.

9. The test strip assembly of claim 1, wherein the wicking membrane is less thick than the lateral flow test strip.

10. The test strip assembly of claim 1, wherein the wicking membrane is less thick than the lateral flow test strip, such that a top of the wicking membrane is further from the dosing window that the lateral flow test strip.

11. A test strip assembly comprising:
    a test strip holder, the test strip holder comprising a base defining a base cavity having a first end and a second end, the base defining a reading window adjacent the second end of the base cavity, the test strip holder further comprising a lid secured to the base over the base cavity, the lid defining a dosing window adjacent the first end of the base cavity;

a wicking membrane received within the base cavity adjacent the first end of the base cavity and aligned under the dosing window; and a lateral flow test strip received within the base cavity, the lateral flow test strip having a dosing end and a testing end, the dosing end being positioned against the wicking membrane, such that an edge of the lateral flow test strip is in line with an edge of the dosing window, wherein the lid is flush with the lateral flow test strip, such that fluid may not flow between the lid and the lateral flow test strip.

12. The test strip assembly of claim 11, wherein the base cavity includes a ledge at the first end of the base cavity, the wicking membrane being positioned between the ledge and the lateral flow test strip, the ledge causing a sample to flow toward the lateral flow test strip from the wicking membrane.

13. The test strip assembly of claim 11, wherein the lid interfaces with the base in a pressure fit arrangement.

14. The test strip assembly of claim 13, wherein the lid includes wings and snaps into the base.

15. The test strip assembly of claim 11, wherein the underside of the lid includes ribs for holding the lateral flow test strip in place.

16. The test strip assembly of claim 15, wherein the lid compresses the lateral flow test strip into the base.

* * * * *